(12) United States Patent
Reglin (10) Patent No.: US 9,186,234 B2
(45) Date of Patent: Nov. 17, 2015

(54) APPARATUS FOR PROMOTING URORECTAL ORGAN EMPTYING AND RELATED METHOD

(71) Applicant: Terell Reglin, Jacksonville, FL (US)

(72) Inventor: Terell Reglin, Jacksonville, FL (US)

(*) Notice: Subject to any disclaimer, the term of this patent is extended or adjusted under 35 U.S.C. 154(b) by 123 days.

(21) Appl. No.: 13/868,156

(22) Filed: Apr. 23, 2013

(65) Prior Publication Data

US 2014/0316381 A1    Oct. 23, 2014

(51) Int. Cl.
| | | |
|---|---|---|
| *A61F 2/00* | (2006.01) | |
| *A61F 5/44* | (2006.01) | |
| *A61F 5/451* | (2006.01) | |
| *A61F 5/455* | (2006.01) | |
| *A61M 25/00* | (2006.01) | |
| *A61F 5/00* | (2006.01) | |
| *A63B 21/02* | (2006.01) | |
| *A63B 23/20* | (2006.01) | |

(52) U.S. Cl.
CPC ............. *A61F 2/0022* (2013.01); *A61F 5/0093* (2013.01); *A61F 5/44* (2013.01); *A61F 5/455* (2013.01); *A61F 5/4553* (2013.01); *A61F 5/4556* (2013.01); *A61M 25/0017* (2013.01); *A61F 2/005* (2013.01); *A61M 2210/1078* (2013.01); *A61M 2210/1092* (2013.01); *A63B 21/028* (2013.01); *A63B 23/20* (2013.01)

(58) Field of Classification Search
CPC ..... A61F 2/0022; A61F 5/4556; A61F 5/455; A61F 2/0004; A61F 2/0031; A61F 2/005; A61F 5/44; A61F 5/4404; A61F 5/4408; A61F 2/0054; A61F 5/4553; A61F 2/0027; A61F 5/0093; A61F 25/0017; A61M 25/0017; A61M 25/00; A61M 25/0009; A61M 2210/1092; A61M 2202/0014; A61M 2202/0496; A61M 2210/1078; A63B 23/20; A63B 21/028; A63B 2213/00; Y10S 128/25

See application file for complete search history.

(56) References Cited

U.S. PATENT DOCUMENTS

| | | | | |
|---|---|---|---|---|
| 2,483,079 | A |  | 9/1949 | Williams |
| 2,638,093 | A | * | 5/1953 | Kulick ............................ 600/29 |
| 3,347,238 | A | * | 10/1967 | Gresham ....................... 604/329 |
| 3,528,423 | A | * | 9/1970 | Lee ............................... 604/329 |
| 3,554,184 | A |  | 1/1971 | Habib |
| 3,661,155 | A |  | 5/1972 | Lindan |
| 3,776,235 | A | * | 12/1973 | Ratcliffe et al. ............... 604/329 |
| 4,139,006 | A |  | 2/1979 | Corey |
| 4,246,901 | A |  | 1/1981 | Frosch et al. |
| 4,568,339 | A | * | 2/1986 | Steer ............................. 604/329 |
| 4,875,898 | A |  | 10/1989 | Eakin |
| 4,889,533 | A |  | 12/1989 | Beecher |
| 5,036,867 | A |  | 8/1991 | Biswas |
| 5,041,077 | A | * | 8/1991 | Kulick ............................ 600/29 |
| 5,049,144 | A |  | 9/1991 | Payton |

(Continued)

FOREIGN PATENT DOCUMENTS

WO    9958169 A2    11/1999

*Primary Examiner* — Adam Marcetich
(74) *Attorney, Agent, or Firm* — The Ollila Law Group (57) ABSTRACT

The invention is directed toward an apparatus for promoting urorectal organ emptying and related method. The apparatus has a funnel that circumscribes a woman's urethral opening and directs urine to pass therethrough and generally away from the woman. A lift portion is attached to the funnel, and is sized to be insertable into the woman's vaginal cavity and displace a prolapsed organ. In the case of prolapsed urinary bladder, the lift portion is shaped to engage the woman's anterior vaginal wall and displace a prolapsed urinary bladder and promote urinal emptying.

20 Claims, 7 Drawing Sheets

(56) References Cited

U.S. PATENT DOCUMENTS

| | | | |
|---|---|---|---|
| 5,785,640 A | 7/1998 | Kresch et al. | |
| 6,394,939 B1 * | 5/2002 | Stein | 482/148 |
| 6,428,521 B1 | 8/2002 | Droll | |
| 6,434,757 B1 | 8/2002 | Filsouf | |
| 6,460,542 B1 | 10/2002 | James | |
| 6,592,560 B2 | 7/2003 | Snyder | |
| 6,676,594 B1 | 1/2004 | Zunker et al. | |
| 2002/0179093 A1 * | 12/2002 | Adamkiewicz | 128/885 |
| 2006/0211911 A1 * | 9/2006 | Jao et al. | 600/29 |
| 2009/0222034 A1 * | 9/2009 | Takashima | 606/197 |
| 2009/0266367 A1 * | 10/2009 | Ziv et al. | 128/834 |
| 2009/0283099 A1 * | 11/2009 | Harmanli | 128/834 |
| 2010/0174214 A1 * | 7/2010 | Gabbay et al. | 601/15 |
| 2010/0256580 A1 * | 10/2010 | Faber | 604/329 |
| 2011/0021870 A1 | 1/2011 | Lee | |
| 2011/0295058 A1 * | 12/2011 | Henriksson et al. | 600/37 |
| 2012/0259163 A1 | 10/2012 | Karapasha | |
| 2013/0138135 A1 * | 5/2013 | Rosen et al. | 606/197 |
| 2013/0150661 A1 * | 6/2013 | Rosen et al. | 600/29 |
| 2014/0243584 A1 * | 8/2014 | Bercovich | 600/29 |
| 2014/0261445 A1 * | 9/2014 | Maaskamp et al. | 128/835 |

\* cited by examiner

APPARATUS FOR PROMOTING URORECTAL ORGAN EMPTYING AND RELATED METHOD

FIELD OF THE INVENTION

The present invention is generally directed toward an apparatus and related method for promoting urinary or rectal emptying in a female having a condition that inhibits urinary or rectal emptying such pelvic organ prolapse.

BACKGROUND

Female Pelvic organ prolapse (FPOP) is a relatively common condition. According to some studies, 75% of women over the age of 18 experience some degree of FPOP. Over 300,000 surgeries are performed annually in the United States. This costs the country more than $20 billion annually in direct and indirect medical costs, while surgeries alone to correct FPOP cost more than $1 billion annually. This condition is projected to become much more common in the United States with the aging of the Baby Boomers. An estimated 11 to 19 percent of women will undergo surgery for FPOP by the age of 80.

Normally pelvic organs are held in place by the muscles and connective tissues of the pelvis. Female Pelvic Organ Prolapse occurs when the pelvic floor muscles are weakened, stretched, or damaged and can no longer support nearby pelvic organs. These pelvic organs can fall (prolapse) from their normal position, and protrude through the vagina. Women commonly complain of discomfort, pressure, incontinence and/or retention and pain in the pelvis. FPOP can also cause bladder and bowel dysfunction. Often, women are unable to fully void their urine and bowl, which can cause leakage and also lead to infection and other health issues. In the most severe cases of FPOP, a visible protrusion of the prolapsed organ through the vaginal introitus can be seen. Risk factors that cause or promote FPOP include: pregnancy and vaginal delivery; surgery such as a hysterectomy that can disrupt the supporting tissues of the pelvis; and other health-related issues such as multiple sclerosis, obesity, aging, and genetics.

Multiple pelvic organs can prolapse, sometimes simultaneously. The organs most often associated with pelvic prolapse include the bladder, rectum, small intestine, and uterus.

There are several different types of FPOP, depending on the organ(s) involved. For example, a cystocele occurs when the bladder protrudes and herniates into the vagina anteriorly. A rectocele describes the protrusion of the rectum through the posterior vaginal wall. An enterocele involves the prolapse of the small intestine into the vagina. Uterine prolapse occurs when the uterus drops into the vagina.

Women suffering from a cystocele may have difficulty emptying their bladder due to the physical obstruction created by the prolapse or tilted bladder. Likewise, those with a rectocele may experience difficulty with emptying stool from the rectum. Such problems may lead to further related health issues, if not addressed.

Treatments to correct FPOP include surgery, physical therapy, and pessaries. Surgery is the most expensive option, requiring the patient to be anesthetized, yet is associated with a high failure rate. Surgery typically entails donor tissue or mesh used to hold the organs in a more upright position. Pessaries are devices that hold the pelvic organs in place and are worn in the vagina 24 hours a day. A pessary typically needs to be removed and cleaned once a month by a doctor. Pessaries are often times accompanied by a hormone prescription. For physical therapy, exercises are performed to strengthen the vaginal vault. This treatment is the least invasive, but is less effective in advanced cases.

Accordingly, the need exists for a simple, yet effective means to overcome the symptoms of pelvic organ prolapse, and in particular to aid in a woman's ability to empty her bladder and/or rectum when voiding. An ideal apparatus for such treatment should be hygienic, portable, reusable, non-toxic, and non-surgical. Additionally, there is a need for a related method for promoting urinary and rectal voiding in women suffering from pelvic organ prolapse.

SUMMARY

In light of the above Background, the present invention provides women suffering from pelvic organ prolapse an apparatus to promote bladder emptying and/or rectal emptying when voiding. An aspect of the apparatus reorients prolapsed pelvic organs into a position that facilitates more complete bladder emptying and/or rectal emptying.

An object of the invention is to reduce the frequency and severity of urinary tract infections in women suffering from pelvic organ prolapse by promoting more complete bladder emptying.

Furthermore, it is an object of the present invention to reduce the physical discomfort experienced during urination and/or defecation by women who suffer from with pelvic organ prolapse.

The invention includes a funnel with a substantially oval-shaped rim. The rim has a ventral edge and a dorsal edge, and the rim defines a first opening. The rim is located proximate an upper portion of the funnel, which is sized and shaped to comfortably rest against a woman's vulva. In this position, the first opening is situated so that it completely surrounds the woman's urethral opening when in use.

The funnel body tapers downward from the upper portion of the funnel and terminates at second opening which is also defined by the funnel body. A conduit is defined by the funnel, and it connects the first opening to the second opening so that urine may pass through the first opening, through the conduit, and out of the funnel via the second opening.

The apparatus also has a generally cylindrical lift portion that is sized and dimensioned to fit into a woman's vaginal cavity and to engage a vaginal wall therein. This lift portion has a distal end, a proximal end, and a shaft portion therebetween. The proximal end of the lift is attached to the dorsal edge of the rim, and the shaft portion extends outwardly from the proximal end. This places the distal end in an orientation so that it can engage a vaginal wall to replace a prolapsed organ into a more anatomic position that is more conducive to better bladder and/or rectal emptying.

In one embodiment of the invention, the funnel is made from a resiliently deformable material so it can flex into engagement with the woman's body. In a related embodiment, the funnel is oriented proximate the woman's vulva when the lift portion is inserted into the woman's vagina. This may be promoted by an arcuately cupped rim.

In yet another embodiment, the apparatus has a shaft that is arcuate. In one embodiment, the lift portion is shaped to engage the woman's anterior vagina to promote displacement of the woman's prolapsed urinary bladder. In yet another embodiment, the lift portion is shaped to engage the woman's posterior vaginal wall adjacent to the lift portion for promoting displacement of the woman's prolapsed rectum.

Another embodiment of the apparatus for promoting urorectal organ emptying comprises a funnel defining first and second openings. The first opening has a size and dimension to circumscribe a woman's urethral opening so it directs urine expelled from the urethral opening to pass therethrough. The funnel has a size and dimension to direct urine expelled from the urethral opening through the second opening and generally away from the woman.

In this embodiment, the lift portion is attached to the funnel, and it projects from the funnel, wherein the lift portion is a size and dimension to be insertable into the woman's vaginal cavity and displace a prolapsed organ. This embodiment is optionally constructed so that the funnel and lift portion are a unibody construction. However, this embodiment is alternately optionally constructed so that the lift portion is removably attached to the funnel.

In a related embodiment, the funnel is made from a resiliently deformable material so as to flex into engagement with the woman's body.

In a related embodiment the shape of the lift portion comprises an enlarged distal portion, and in another variation, the lift portion comprises a generally serpentine shaft portion, and a tapered distal portion. The lift portion comprises an arcuate segment in an alternate embodiment.

This apparatus for promoting urorectal organ emptying further, in yet another embodiment, comprises a rim with the funnel that circumscribes the top opening and the rim has a shape and dimension to engage the woman's vulva. The rim can be arcuately cupped. In a rimmed embodiment, the lift portion projects outwardly from the rim of the funnel.

The apparatus alternately comprises a lift portion shaped to engage the woman's anterior vaginal wall and displace prolapsed urinary bladder. In a related variation, the lift portion is shaped to engage the woman's posterior vaginal wall and displace a prolapsed rectum.

The invention also contemplates a method for promoting bladder and bowel emptying in a woman comprising the steps of inserting a lift portion inside the woman's vaginal cavity, displacing a prolapsed organ adjacent to the vaginal wall with the lift portion, and providing a funnel of a size and dimension to engage a woman's vulva, the funnel having a size and dimension to direct urine expelled from the woman's urethral opening generally away from the woman. In a preferred embodiment of the method, the lift portion is attached to the funnel.

The apparatus contemplated by the invention can be used either standing or sitting, and is not limited to women with FPOP. It can be used by any female with a vaginal opening. Women who are poor candidates for surgery or women for whom surgery has failed can also benefit from use of the invention. Women in need of relief from incontinence issues may also benefit. Additionally, women suffering from multiple sclerosis, arthritis, obesity, aging or other health issues that make standing to urinate a more fitting option than sitting may also benefit from the invention.

Elderly women with urinary tract infections who must often make multiple trips to the bathroom, day and night, are at a higher risk for slips and falls. Additionally, using the toilet and having to sit down and get up more often can cause joint pain, discomfort, and can become tiresome. The apparatus contemplated herein helps reduce the frequency of urination by allowing a more complete bladder emptying.

The device is flexible, discrete, and portable. It is easy to use, easy to clean, and hygienic. It can be used as needed. No lubrication or condom is necessary for use, but may be used as desired. The device is waterproof and can be used in the shower, outdoors, or any restroom. It can be used sitting or standing. A wide range of sizes for all grades of prolapse is contemplated by the present invention.

Compared to surgery, the invention is non-evasive, painless, and inexpensive. It may be used in the comfort of one's own home. Compared to a pessary, the device is only used while voiding and does not require ongoing care of a physician. When used properly the device is not associated with any vaginal discharge or infection.

BRIEF DESCRIPTION OF THE DRAWINGS

For a fuller understanding of the invention, reference is made to the following detailed description, taken in connection with the accompanying drawings illustrating various embodiments of the present invention, in which.

DETAILED DESCRIPTION OF EMBODIMENTS OF THE INVENTION

In the Summary above and in the Description of Embodiments of the Invention, reference is made to particular features (including method steps) of the invention. It is to be understood that the disclosure of the invention in this specification includes all possible combinations of such particular features, regardless of whether a combination is explicitly described. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other features or steps are optionally present. When reference is made herein to a method comprising two or more defined steps, the steps can be performed in any order or simultaneously (except where the context excludes that possibility), and the method can include one or more steps which are carried out before any of the defined steps, between two of the defined steps, or after all of the defined steps (except where the context excludes that possibility).

This invention may be embodied in many different forms and should not be construed as limited to the embodiments set forth herein. Rather, these embodiments are provided so that this disclosure will be thorough and complete, and will convey the scope of the invention to those skilled in the art. Other related embodiments will be known and understood by those of ordinary skill in the art now having the benefit of the teachings of the present invention.

Embodiments of the invention are described herein in connection with an apparatus for promoting urorectal organ emptying in women having difficulty with urorectal organ emptying, such as women suffering from pelvic organ prolapse. It is to be understood, however, that the invention is not limited to the specific sizes, shapes, or medical conditions described.

The Apparatus

Figure 1:
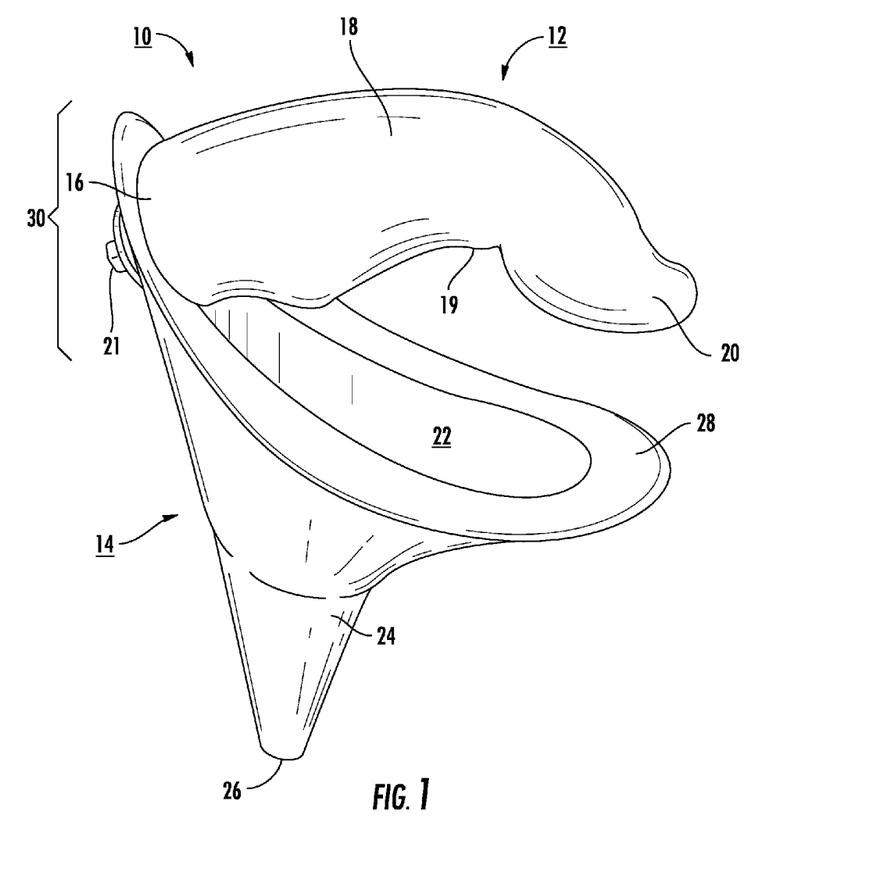
FIG. 1 illustrates a perspective view of an embodiment of an apparatus for promoting urorectal organ emptying.
Figure 2:
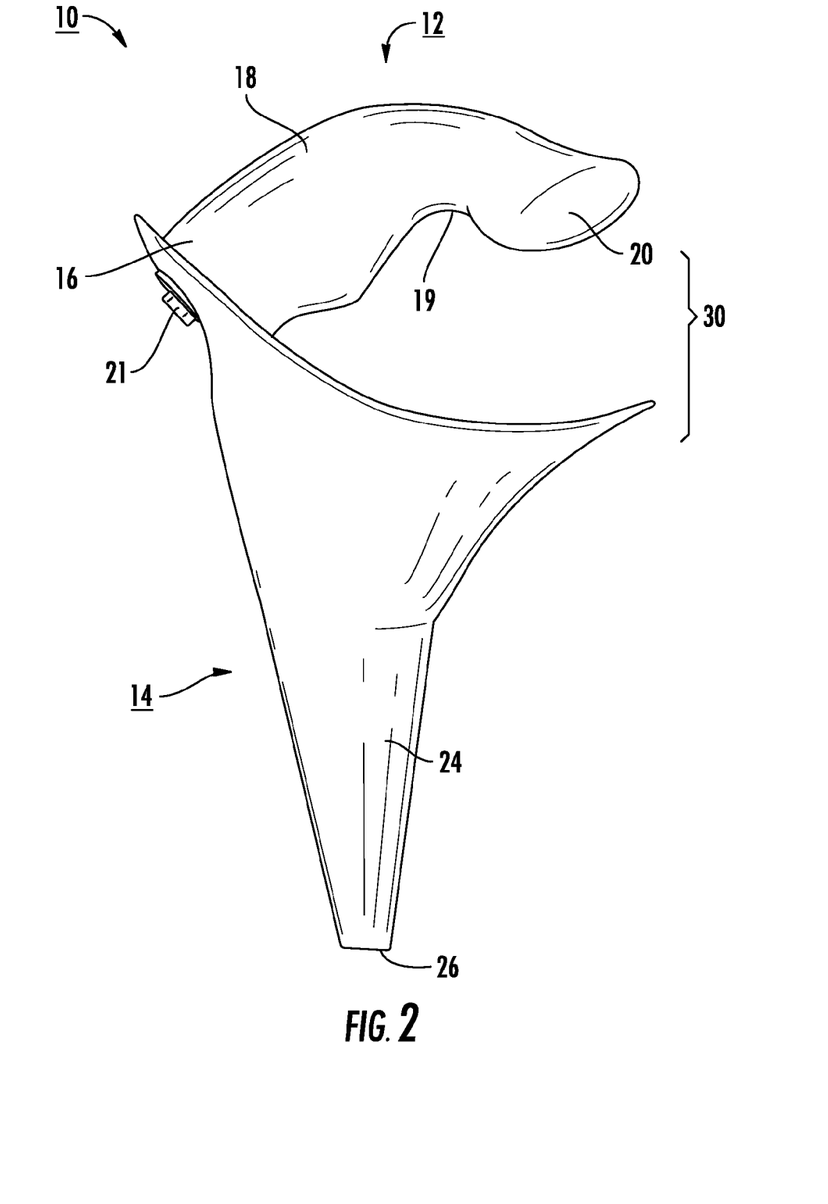
FIG. 2 illustrates a side view of the apparatus illustrated in FIG. 1.
Figure 3:
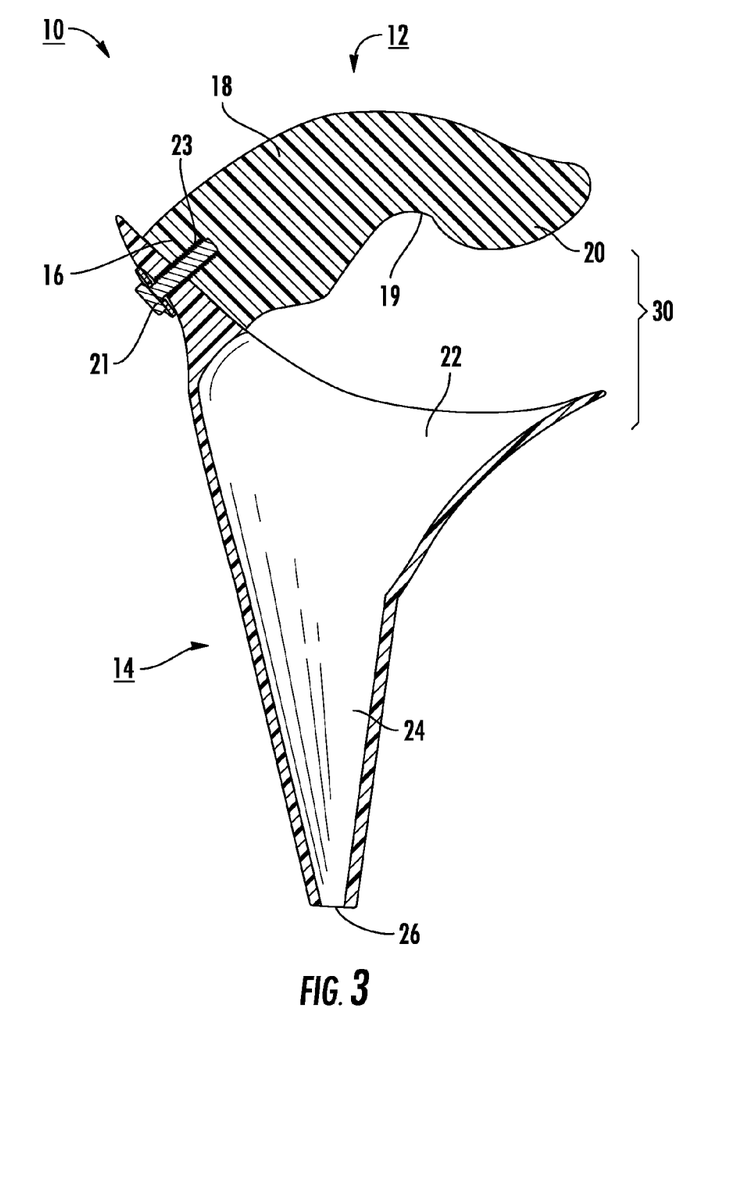
FIG. 3 illustrates a side cutaway view of the apparatus illustrated in FIGS. 1 and 2.

FIGS. 1, 2 and 3 illustrate one embodiment of an apparatus 10 contemplated by the invention. In this embodiment, a lift portion 12 is attached to a funnel 14. The lift portion 12 is generally cylindrical, and is sized to be insertable into a woman's vaginal cavity and contact at least one vaginal wall therein. The lift portion 12 has proximal end 16 that is attached to the funnel 14. A shaft portion 18 projects from the proximal end 16 and terminates in a distal end 20. In one embodiment, the shaft portion 18 is oriented to engage a vaginal wall to displace a prolapsed organ adjacent thereto. In one embodiment, the distal end 20 is oriented to engage a vaginal wall to displace a prolapsed organ adjacent thereto. The shaft portion 18 is substantially straight in one embodiment, and in an alternate embodiment, the shaft portion 18 comprises at least one arcuate region 19.

Figure 4:
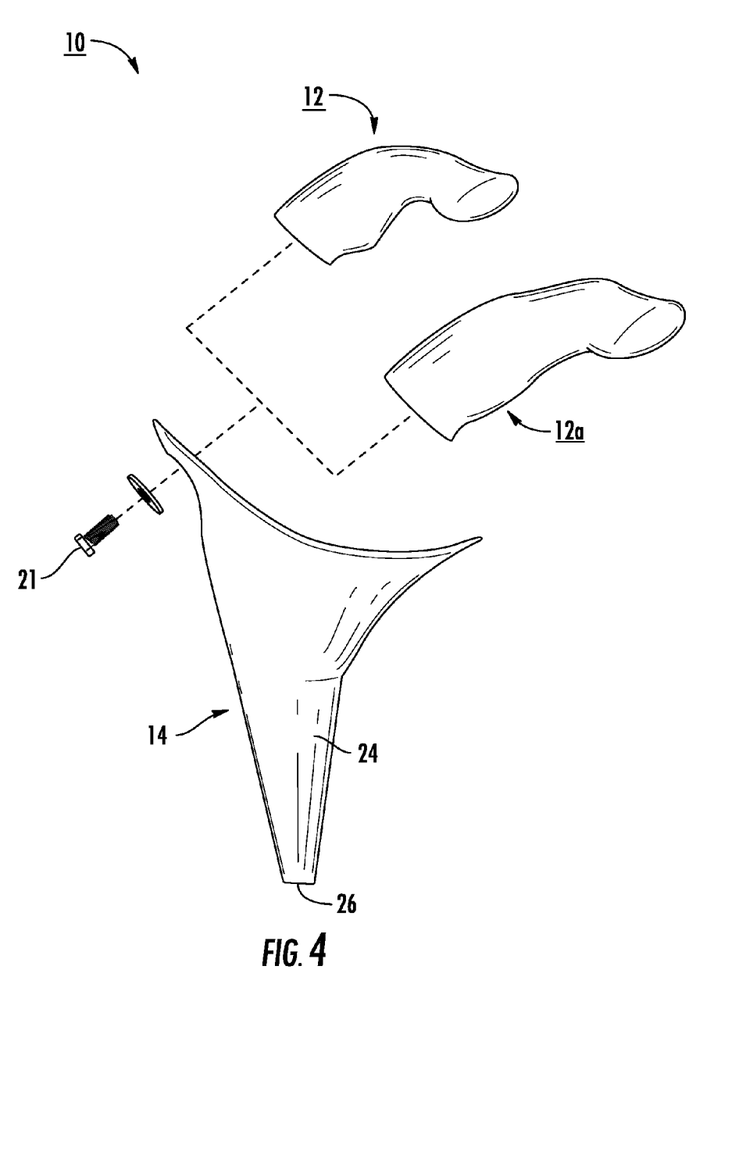
FIG. 4 illustrates a side view of an alternate embodiment of the apparatus illustrated in FIGS. 1, 2 and 3.

FIGS. 3 and 4 illustrate the lift portion 12 attaching to the funnel 14 with a fastener 21. Any fastener known in the art is contemplated. In one embodiment, however, a threaded fastener engages mating threads 23 of the lift portion to secure the lift portion 12 to the funnel 14. Besides mechanical fasteners, in an alternate means of attachment, adhesive affixes the lift portion 12 to the funnel 14. Additionally, welding or melting the lift portion 12 to the funnel 14 is also contemplated.

Figure 5:
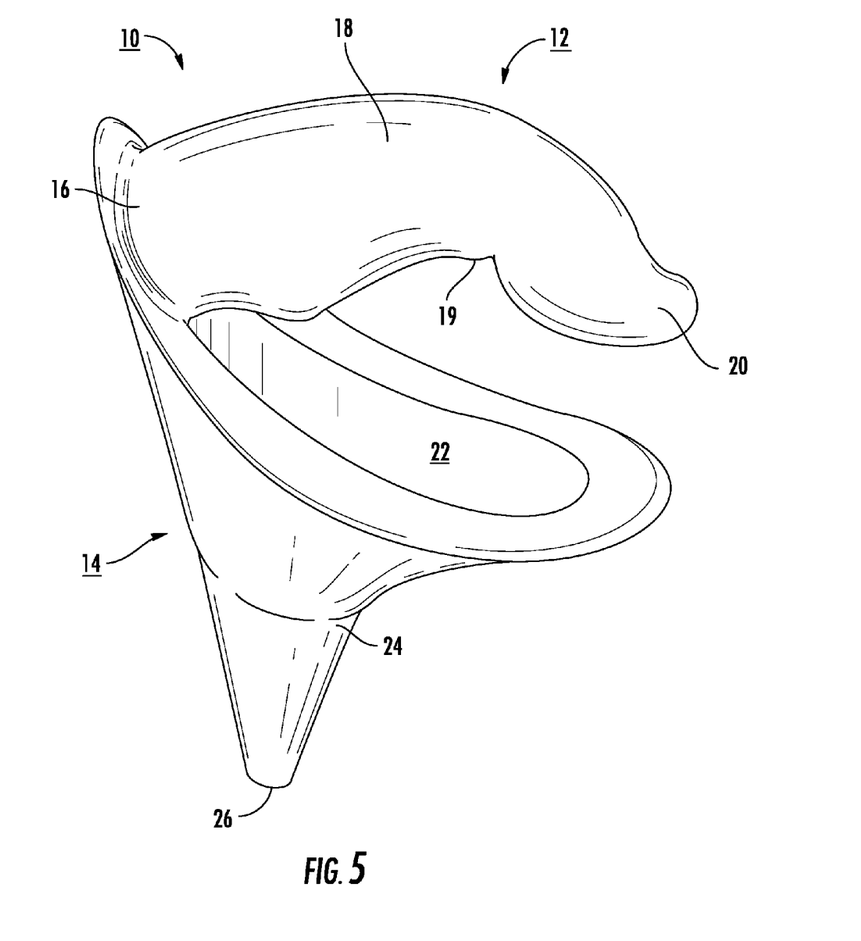
FIG. 5 illustrates a perspective view of an embodiment of an apparatus for promoting urorectal organ emptying wherein the apparatus is a unibody construction.

FIG. 5 illustrates an embodiment of the invention wherein the lift portion 12 is molded with the funnel 14 as a unibody construction.

FIG. 4 additionally illustrates the interchangeable nature of the lift portion 12 in a preferred embodiment. Due to human anatomical variations in size and morphology, lift portions are contemplated in multiple size ranges to accommodate different women. Besides alternate sizes to accommodate biological variation, the lift portion 12 is contemplated in varying morphology (12a, illustrated as an example) to accommodate biological variations in vaginal anatomy. Additionally, shapes vary to favorably target engaging a particular (e.g. anterior or posterior) wall of the vagina. The lift portion 12 has at least one of a round, oval, oblate, and polygonal cross sectional shape. The shaft portion 18 is at least one of straight, arcuate, and serpentine. The distal end 20 is at least one of bulbous, tapered, rounded, and flat.

Turning back to FIGS. 1, 2 and 3, the funnel 14 is of a size and dimension to comfortably engage a woman's vulva. In particular, a first opening 22 is shaped and positioned to circumscribe a woman's urethral opening when the funnel is placed against a woman's vulva. Should a woman urinate into the funnel 14, the urine passes through the first opening 22, into a conduit 24 defined by the funnel 14, and out of the funnel 14 through a second opening 26. In a preferred embodiment, the conduit 24 is a generally tapered shape that points in a direction that directs urine away from the woman's body. In a preferred embodiment, the funnel made of a resiliently deformable material so that it may comfortably flex into engagement with the woman's body.

FIGS. 1 and 2 also illustrate one embodiment of the funnel 14 wherein a rim 28 having a substantially oval shape defines the first opening 22. The rim 28 is proximate an upper portion 30 of the funnel, and it is this upper portion that preferably contacts the woman's vulva. In a preferred embodiment, the rim 28 is arcuately cupped to accommodate a woman's vulva. In the embodiment depicted by FIGS. 1 and 2, the lift portion 12 is attached proximate the rim 28. However, the lift portion is also contemplated to project from any exterior or interior surface of the funnel 14.

The lift portion 12 and funnel 14 are each preferably made from a relatively compliant yet resilient material, such as rubber, latex, nitrile, silicone, methyl vinyl silicone, phenyl methyl silicone, platinum cure silicone, fluorocarbon elastomer, perfluorinated elastomer, acrylate, nitrile, hydrogenated nitrile butadiene rubber, and any other relatively compliant material known in the art.

However, materials may also be chosen such as plastics, high density polyethylene, low density polyethylene, polyethylene terephthalate, Nylon, Polystyrene styrenic block copolymer, thermoplastic polyester elastomer, aliphatic polyether-based thermoplastic polyurethane, elastomeric thermoplastic polyurethane, polyolefins, polyamide nylon, metallocene polyethylene resins, polyether block amide, polyvinyl chloride, polyurethane, polypropylene, polyoxymethylene, polystyrene, post-consumer resin, K-resin, epoxy resin, phenolic formaldehyde resin, stainless steel, aluminum, other metals, ceramic, glass, and any other material known in the art.

The lift portion 12 is, in one embodiment constructed from a solid piece of material, but in an alternate embodiment, comprises a hollow cavity within. The lift portion 12 may, in an alternate embodiment, also be constructed of multiple materials. For example, a core material may comprise an overmolded material disposed thereon. Similarly, the funnel 14 may, in an alternate embodiment, comprise portions constructed from different materials.

The Apparatus in Use

Figure 6:
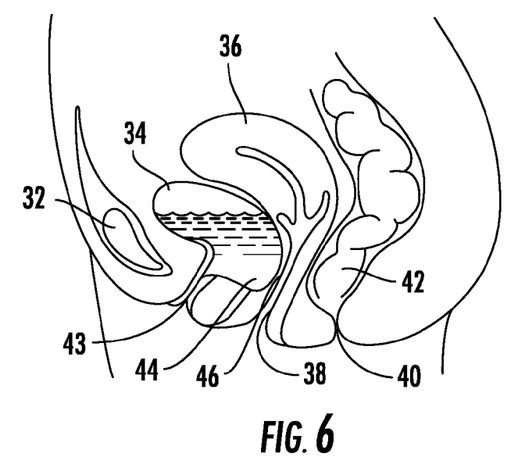
FIG. 6 illustrates a side cutaway view of typical female pelvic anatomy in a woman experiencing bladder prolapse (cystocele)

FIG. 6 is a schematic that illustrates typical female pelvic anatomy in a woman experiencing bladder prolapse (cystocele). The pelvic anatomy illustrated includes the pubic bone 32, bladder 34, uterus 36, vagina 38, anus 40, rectum 42, and urethral opening 43. FIG. 6 indicates a region of bladder prolapse 44 wherein the bladder 34 bulges or herniates into the vagina 38.

Figure 7:
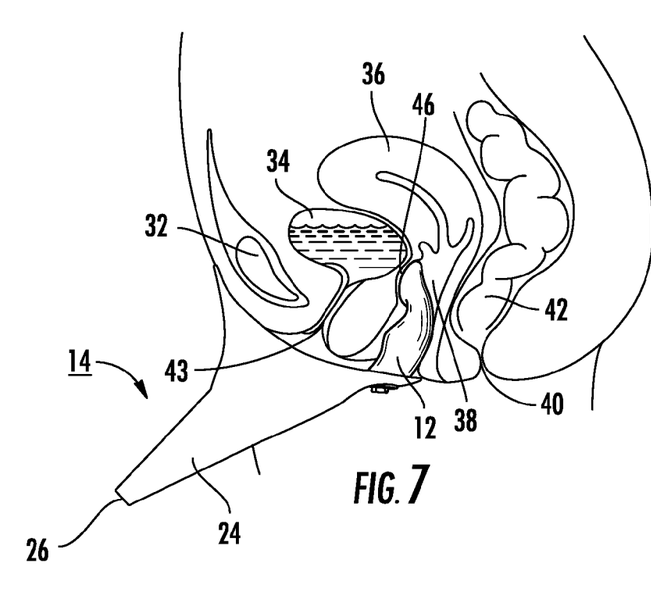
FIG. 7 illustrates a side cutaway view of typical female pelvic anatomy in a woman experiencing bladder prolapse (cystocele) with an embodiment of an apparatus for promoting urorectal organ emptying in use.

FIG. 7 illustrates a woman experiencing bladder prolapse (cystocele), but has the apparatus 10 inserted into her vagina 38. The lift portion 12 applies pressure to the anterior vaginal wall 46 and displaces the bladder 34. This has the effect of raising the bladder 34 above the urethral opening 43, thus allowing fuller emptying of the bladder 34 upon urination. When the lift portion 12 is inserted into the woman's vagina 38, the funnel 14 attached to the lift portion 12 is positioned to catch any urine expelled from the urethral opening 43 and direct the urine away from the woman's body. This allows the woman to urinate in a sitting or standing position.

Figure 8:
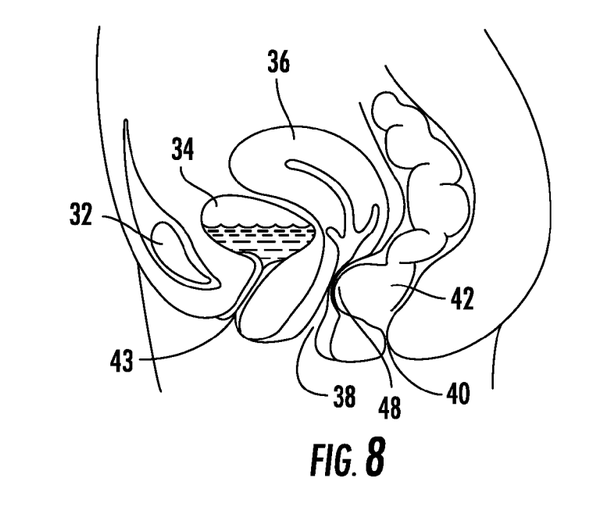
FIG. 8 is a side cutaway view that illustrates typical female pelvic anatomy in a woman experiencing rectal prolapse (rectocele)

FIG. 8 is a schematic that illustrates typical female pelvic anatomy in a woman experiencing rectal prolapse (rectocele). The pelvic anatomy illustrated also includes the pubic bone 32, bladder 34, uterus 36, vagina 38, anus 40, rectum 42, and urethral opening 43. FIG. 8 indicates a region of rectal prolapse 48 wherein the rectum 42 bulges or herniates into the vagina 38.

Figure 9:
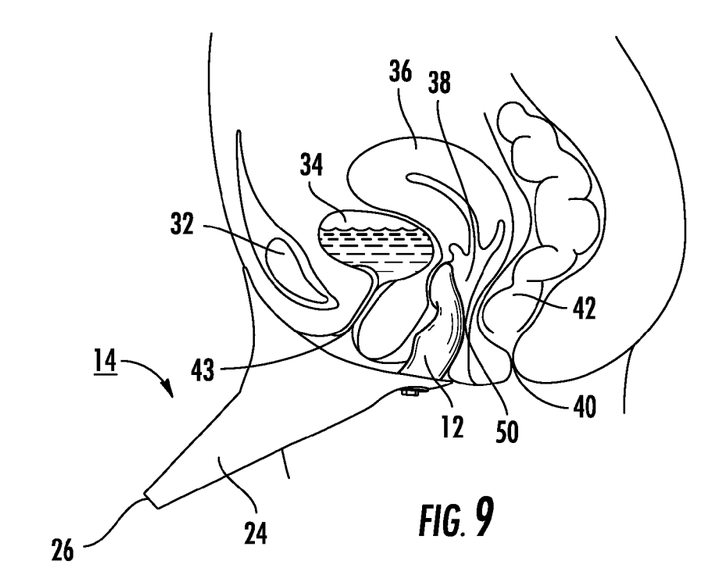
FIG. 9 illustrates a side cutaway view of typical female pelvic anatomy in a woman experiencing rectal prolapse (rectocele) with an embodiment of an apparatus for promoting urorectal organ emptying in use.

FIG. 9 illustrates a woman experiencing rectal prolapse (rectocele), but has the apparatus 10 inserted into her vagina 38. The lift portion 12 applies pressure to the posterior vaginal wall 50 and displaces the rectum 42. This has the effect of relieving pressure on the rectum 42 proximate the anus 40, and allowing fuller emptying of the rectum 42 upon defecation. When the lift portion 12 is inserted into the woman's vagina 38, the funnel 14 attached to the lift portion 12 is positioned to catch any urine expelled from the urethral opening 43 and direct the urine away from the woman's body. This allows the woman to urinate in a sitting or standing position.

Method of Promoting Bladder and Bowel Emptying

The invention contemplates a method of promoting bladder and bowel emptying in a woman in need thereof. Referring to FIGS. 6-9 for illustrative purposes, in a preferred embodiment a lift portion 12 is inserted into a woman's vaginal cavity 38. This causes pressure to be applied by the lift portion 12 to a vaginal wall therein, resulting in displacing a prolapsed organ adjacent to the vaginal wall. This relieves pelvic organ pressure, and facilitates urination and/or defecation. For example, as illustrated by FIGS. 6 and 7, in a woman suffering from cystocele (urinary bladder prolapse), the lift portion 12 applies pressure to the anterior vaginal wall 46 and displaces the prolapsed bladder 44, thus restoring pelvic anatomy to a more optimal physiological position.

The method also contemplates providing a funnel of a size and dimension to engage a woman's vulva. The funnel is sized and dimensioned to direct urine expelled from the woman's urethral opening to pass through the funnel and generally away from the woman. This allows a woman to sit or stand while urinating, for some women suffering from pelvic organ prolapse may have difficulty or discomfort from squatting or sitting during urination. In a preferred embodiment of the method for treating pelvic organ prolapse the lift portion 12 is attached to the funnel 14.

The invention claimed is:

1. An apparatus for promoting urorectal organ emptying comprising:
   a funnel having an substantially oval-shaped rim, the rim having a ventral edge and a dorsal edge, wherein the rim defines a first opening, wherein the rim is proximate an upper portion of the funnel, wherein the upper portion is of a size and dimension to engage a woman's vulva and the first opening is disposed to circumscribe the woman's urethral opening when in use;
   a generally tapering funnel body extending away from the upper portion of the funnel;
   a second opening defined by the funnel body;
   a conduit defined by the funnel, the conduit connecting the first opening to the second opening so that urine may pass therethrough;
   a generally cylindrical lift portion having a size and dimension to fit into a woman's vaginal cavity and engage a vaginal wall therein, wherein the lift portion comprises a distal end, a proximal end, and a shaft portion therebetween, wherein the proximal end of the lift is attached proximate the dorsal edge of the rim, wherein the shaft portion extends outwardly from the proximal end, wherein the distal end is oriented to engage the vaginal wall to displace a prolapsed organ adjacent thereto when in use, wherein the lift portion comprises an arcuate segment, and wherein the distal end is shaped to engage the woman's anterior vaginal wall to promote displacement of a prolapsed urinary bladder, and the shaft portion is shaped to engage the woman's posterior vaginal wall for promoting displacement of a prolapsed rectum; and
   a hump on the proximal end of the lift portion that protrudes anteriorly to engage the vaginal wall when in use.

2. The apparatus for promoting urorectal organ emptying of claim 1, wherein the funnel is made from a resiliently deformable material so as to flex into engagement with the woman's body when in use.

3. The apparatus for promoting urorectal organ emptying of claim 1, wherein the lift portion comprises a solid piece of material.

4. The apparatus for promoting urorectal organ emptying of claim 1, wherein the lift portion is tapered, such that the distal end of the lift portion is smaller than the proximal end of the lift portion.

5. An apparatus for promoting urorectal organ emptying comprising:
   a funnel defining first and second openings, the first opening having a size and dimension to circumscribe a woman's urethral opening and direct urine expelled from the urethral opening to pass therethrough, the funnel having a size and dimension to direct urine expelled from the urethral opening through the second opening and generally away from the woman; and
   a lift portion attached to the funnel, the lift portion projecting from the funnel, wherein the lift portion is a size and dimension to be insertable into the woman's vaginal cavity and displace a prolapsed organ.

6. The apparatus for promoting urorectal organ emptying of claim 5, wherein the funnel is made from a resiliently deformable material so as to flex into engagement with the woman's body when in use.

7. The apparatus for promoting urorectal organ emptying of claim 5, wherein the funnel and lift portion are a unibody construction.

8. The apparatus for promoting urorectal organ emptying of claim 7, wherein the lift portion comprises a generally serpentine shaft portion, wherein the shaft portion is configured to be disposed more posteriorly than any other region of the lift portion when in use.

9. The apparatus for promoting urorectal organ emptying of claim 7, further comprising a rim with the funnel that circumscribes the first opening, the rim having a shape and dimension to engage the woman's vulva.

10. The apparatus for promoting urorectal organ emptying of claim 9, wherein the rim is arcuately cupped.

11. The apparatus for promoting urorectal organ emptying of claim 9, wherein the lift portion projects outwardly from the rim of the funnel.

12. The apparatus for promoting urorectal organ emptying of claim 5, wherein the lift portion is removably attached to the funnel.

13. The apparatus for promoting urorectal organ emptying of claim 5, wherein the lift portion comprises an enlarged distal portion.

14. The apparatus for promoting urorectal organ emptying of claim 5, wherein the lift portion is shaped to engage the woman's anterior vaginal wall and displace a prolapsed urinary bladder when in use.

15. The apparatus for promoting urorectal organ emptying of claim 5, wherein the lift is shaped to engage the woman's posterior vaginal wall and displace a prolapsed rectum when in use.

16. A method for promoting bladder and bowel emptying in a woman comprising the steps of:
   inserting a lift portion inside the woman's vaginal cavity, wherein the lift portion comprises an arcuate segment wherein a hump proximate a proximal end of the lift portion protrudes anteriorly to engage the vaginal cavity;

displacing a urinary bladder with a distal end of the lift portion; and displacing a prolapsed rectum with a shaft portion shaped to engage the woman's posterior vaginal wall for promoting displacement of a prolapsed rectum;

providing a funnel of a size and dimension to engage a woman's vulva, the funnel having a size and dimension to direct urine expelled from the woman's urethral opening generally away from the woman.

17. The method for promoting bladder and bowel emptying of claim 16, wherein the lift portion is attached to the funnel.

18. The method for promoting bladder and bowel emptying of claim 16, wherein the lift portion comprises a solid piece of material.

19. The method for promoting bladder and bowel emptying of claim 16, wherein the shaft portion is configured to be disposed more posteriorly than any other region of the lift portion when inside the woman's vaginal cavity.

20. The method for promoting bladder and bowel emptying of claim 16, wherein the lift portion is tapered, such that the distal end of the lift portion is smaller than the proximal end of the lift portion.

* * * * *